(12) United States Patent
Thompson (10) Patent No.: US 6,358,708 B1
(45) Date of Patent: Mar. 19, 2002

(54) CANDIDA ALBICANS SRB-7

(75) Inventor: Craig M. Thompson, Arlington, MA (US)

(73) Assignee: Anadys Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/495,066

(22) Filed: Jan. 31, 2000

Related U.S. Application Data
(60) Provisional application No. 60/118,604, filed on Feb. 4, 1999.

(51) Int. Cl.$^7$ .................................................. C12P 21/02
(52) U.S. Cl. ................ 435/69.1; 435/320.1; 435/254.2; 435/254.21; 435/254.4; 435/358; 435/367; 435/410
(58) Field of Search ............................. 536/23.1, 23.72, 536/23.74; 530/350, 371; 435/320.1, 69.1, 254.2, 254.21, 254.4, 358, 367, 410

(56) References Cited

U.S. PATENT DOCUMENTS 5,585,277 A   12/1996   Bowie et al. ................ 436/518
5,679,582 A   10/1997   Bowie et al. ................ 436/518

FOREIGN PATENT DOCUMENTS

| WO | WO 97/20952 | 6/1996 |
| WO | 97 08301 | 3/1997 |
| WO | WO 97/09301 | 3/1997 |
| WO | 97 36925 | 10/1997 |
| WO | 97 37230 | 10/1997 |

OTHER PUBLICATIONS

J.P. Tam. *Proc. Natl. Adad Sci.* USA 85:5409–5412, 1988.
R,M. Breyer and R.T. Sauer, *J. Biol. Chem.*, 264(5): 13348–13354, 1989.
A.J. Koleske and R.A. Young, *Nature* 368:466–469, 1994.
Chao, David M, et al. "A mammalian SRB protein associated with an RNA polymerase II holoenzyme" Nature (London) 1996, vol, 380, No. 6569, pp. 82–85.

*Primary Examiner*—James Ketter
(74) *Attorney, Agent, or Firm*—Darby & Darby (57) ABSTRACT

Disclosed herein is a purified isolated nucleic acid encoding *Candida Albicans* SRB-7 (CaSRB-7) and an isolated polypeptide encoded by said nucleic acid. Also disclosed herein are vectors comprising the nucleic acid sequences, cells comprising the vectors, methods for producing the polypeptides and methods of use thereof.

6 Claims, 5 Drawing Sheets

```
  1 agtttaaaaatagcctgatatatcaataggataggatgggatgggaggggaggtaatgagttga  80
 81 aggaagaagtaaatacaaaagaactaaaaaattgggttgaactgtgaataaatgtaatttcgataagaatga 160
161 atcaaatccaaatactattgtagaataaagatatatctctttttagttatataaccttttctatcaattaa 240
241 agaaaggggactaaacagaaaatgggaaagatcaataaattgtgggaatcaatcagtgaaagaagaaga 320
321 agaagagaaagtcctgccctccaccccccgccctcgtattacataatcaacatataacgttattatca 400
401 tcagcattgcctatttgaatctagcacgtgatattacacaacacagaattgcttctgcacgaccttac 480
481 ttaacacttgaatcaaaaaaagttcacacacaatattgaaaagttcaatccaactatacaccaagaccaact 560
561 taacccaacattcctta att ATG GCA GAT AGA TTA ACT CAA ATT TGT TTA GAC CAG CTA 625
  1                   M   A   D   R   L   T   Q   I   C   L   D   Q   L   15

626 ATT CAA CAA TTC AAT TCA ACG ATA AAT TAT GTC AAT ACC AGT GCC GAA CCC AGT CTA TTA 685
 16  I   Q   Q   F   N   S   T   I   N   Y   V   N   T   S   A   E   P   S   L   L  35

686 GAT GAC GAT GAT GTC AAC TCC TAT TCC AAT ATG GCA GCT AAT GCC CCA TTG CCA CAA TCC 745
 36  D   D   D   D   V   N   S   Y   S   N   M   A   A   N   A   P   L   P   Q   S  55

746 CAA CAA CAA CAA CGG CAA CAA AAG CAA CAA CAG GAA CCA CAA GAA ATA GAA CAA CCA 805
 56  Q   Q   Q   Q   R   Q   Q   K   Q   Q   Q   E   P   Q   E   I   E   Q   P  75

806 CAA CAA CAA AGT AAC CCT GAA TCA AAG AGT ATT TCT CCG CCA AAA GAA AAA GTG AGT TTT 865
 76  Q   Q   Q   S   N   P   E   S   K   S   I   S   P   P   K   E   K   V   S   F  95

866 GAT AAT GTA ATC AAT GAG TTA TGC ACA GAT TTA ATT TTG AAA AGT CGA CAA ATC AAA ATG 925
 96  D   N   V   I   N   E   L   C   T   D   L   I   L   K   S   R   Q   I   K   M  115
```

FIG. 2B

```
 926 TTA ATT GAT TCA TTA CCT GGT ATA GGA GTT ACA CCC AAT GAA CAA ATG AAT CTA ATC AAT  985
 116  L   I   D   S   L   P   G   I   G   V   T   P   N   E   Q   M   N   L   I   N   135

986 GAA TTA AGT GAT AAA TTG CAA GCT ATA GAA GAA AGA ATT CAA AAA ATC AAA GAA AAA 1045
 136  E   L   S   D   K   L   Q   A   I   E   E   E   R   I   Q   K   I   K   E   K  155

1046 GAT AAT CTA TTA AAT CTA TTA GAA AGT ATG ATT AAA GAG GTA GTT AAT GGT ATA ACC GAA 1105
 156  D   N   L   L   N   L   L   E   S   M   I   K   E   V   V   N   G   I   T   E   175

1106 ACA AGA ATA TGA taaaaaagaaatactttcagcttctctattgttctcccccctctattaacctgtatatgtc 1181
 176  T   R   I   *                                                                     179

1182 atacaatcaatgtcccaatttggaaaccatttatgagaattacattgatctaatgtccatgcaatccatatgtgattgg 1261
1262 tataaattcataaaagcagtatattgcactgacaaatattgttgcagtattatacaccaataatttgttttttagcga 1341
1342 cacgataattcaaatattgacttaataataattccaaaattaatgatgccagtaaaattgatgtaaatataagtttctt 1421
1422 gacatgagacaataaggaatataaccatcccaccaaatatggccagaattgttgtaaagttggcatatgg 1501
1502 tgatgattggatgatgatggaggagatgcataaggtttaacttatataaacgataaacgacatttgaatatagcta 1581
1582 ttaaacccacaaaaataccagataataaatggcaacattcctaaataatataaatagacttgattcttcatcgattgat 1661
1662 ttcaaattgta 1672
```

FIG. 3

```
1   MADRLTQICLDQLIQQFSTNYVNTSAEPSLDDDDV        CaSRB7
1   MTDRLTQLICLDQMTEQFCATLNYIDKN-------       ScSRB7
1   MADRLTQLQDAVNSLADQFCNAIGVLQQGPPA---       HuSRB7

41  NSYSNMAANAPLFQSQQQRQQQKKQEPQQFIEQPQQQQSN  CaSRB7
30  HGFERLTVNEP-----QMSDKHA------             ScSRB7
34  -SFNN-----------QTAINKDQPANPEE----        HuSRB7

81  PESKSISPPKEKVSFPNVINELCFQIIKSRQIKMIIDSL   CaSRB7
48  ----TVVPPEI--FSNTIDELSTDIILKTRQINKLIDSL   ScSRB7
54  -----------YAQLFAAL--IARTAKDIDVLIDSL      HuSRB7

121 PGGVFPNEQMNINELSDKLRIEEERIQKIKEKDNLN      CaSRB7
81  PGVDVSAFEQLRKIDMLQKKLEVEDEKEAIKKEKLLR     ScSRB7
77  PSEESTAALDAASLYKLEEENHAATCVEDVVYRGDMLLE   HuSRB7

161 LLESMIREVVNGITETR-I                       CaSRB7
121 HVDSIIEDFYDGIANSKKST                      ScSRB7
117 KIQSALADIAQSQLKTRSGTHSQSLPDS              HuSRB7
```

Decoration 'Decoration #1': Box residues that match the Consensus exactly.

FIG. 4

Lane

1. SRB7/SRB7 (CAI8)
2. SRB7 / Δsrb7::ADE2 (SHC1)
3. SRB7 / Δsrb7::URA3 (SHC2)
4-8. SRB7 / Δsrb7::ADE2, Ura+

SEQUENCE LISTING

<160> NUMBER OF SEQ ID NOS: 10

<210> SEQ ID NO 1
<211> LENGTH: 1672
<212> TYPE: DNA
<213> ORGANISM: Candida albicans

<400> SEQUENCE: 1

```
agtttaaaaa tagcctgata tatcaatagg ataggatagg ttaggatggg atgggaaggg      60
aggggagggt aatgagttga aggaagaagt aaatacaaaa taaggaactt aaaaaaattg     120
ggttgaaact gtgaataaat ggtaatttcg ataagaatga atcaaatcca aataataact     180
attattgtag aataaagata tatatctctt ttttagttat aaacctttct tatcaattaa     240
agaaaggggg aactaaacag aaaaatgggg gaaagattaa taaattgtgg gaatcaatca     300
aatcagctga aagaagaaga agaagaagaa gaaagtcctg cccttccacc cctcccccg     360
cgccctcgta ttacataatc aacattaaac gttattatca tcagcattgc cttatttgga     420
aatctagcac gtgatattac ataaacacaa cacagaattg gcttctgcac acgaccttac     480
ttaacacttg aatcaaaaaa aaaaaagtc acaacaacaa tattgaaaag ttcaatccaa     540
cctatacacc aagaccaact taacccaaca ttccttaatt atggcagata gattaactca     600
attacaaatt tgtttagacc agctaattca acaattcaat tcaacgataa attatgtcaa     660
taccagtgcc gaacccagtc tattagatga cgatgatgtc aactcctatt ccaatatggc     720
agctaatgcc ccattgccac aatcccaaca acaacggcaa caacaaaaga aacaacagga     780
accacagcaa gaaatagaac aaccacaaca acaaagtaac cctgaatcaa agagtatttc     840
tccgccaaaa gaaaaagtga gttttgataa tgtaatcaat gagttatgca cagatttaat     900
tttgaaaagt cgacaaatca aaatgttaat tgattcatta cctggtatag gagttacacc     960
caatgaacaa atgaatctaa tcaatgaatt aagtgataaa ttgcaagcta tagaagaaga    1020
aagaattcaa aaaatcaaag aaaaagataa tctattaaat ctattagaaa gtatgattaa    1080
agaggtagtt aatggtataa ccgaaacaag aatatgataa aaaagaaat actttcagct    1140
tctattgttc tccccccccc tctatttaac ctgtatatgt catacaatca atgtcccaat    1200
ttggaaacca tttatgagaa ttacattgat ctaatgtcca tggcaatcca tatgtgattg    1260
gtataaattc ataaaagcag tatattgcac tgacaaatat tgttgcagtt attataccac    1320
caataatttt gttttagcg acacgataat tcaaatattg acttaataat aatattccaa    1380
aatttaatgc cagtaaataa tgatgtaaat ataagtttct tgcatgaga caataaggaa    1440
tataattaat aaaccatccc accaaatatg gccaggaatt gttgtaaaag ttggcatatg    1500
gtgatgattt ggatgatgat ggaggagatg cataagggtt taactttata aacgaataaa    1560
```

```
tggcacattt gaatatagct attaaaccca caaaaaatac cagataataa atggcaacat    1620
ttcctaaata ataaaataga cttgattctt catcgattga tttcaaattg ta           1672
```

<210> SEQ ID NO 2
<211> LENGTH: 178
<212> TYPE: PRT
<213> ORGANISM: Candida albicans

<400> SEQUENCE: 2

```
Met Ala Asp Arg Leu Thr Gln Leu Gln Ile Cys Leu Asp Gln Leu Ile
 1               5                  10                  15

Gln Gln Phe Asn Ser Thr Ile Asn Tyr Val Asn Thr Ser Ala Glu Pro
            20                  25                  30

Ser Leu Leu Asp Asp Asp Val Asn Ser Tyr Ser Asn Met Ala Ala
        35                  40                  45

Asn Ala Pro Leu Pro Gln Ser Gln Gln Arg Gln Gln Lys Lys
    50                  55                  60

Gln Gln Glu Pro Gln Gln Glu Ile Glu Gln Pro Gln Gln Ser Asn
65                  70                  75                  80

Pro Glu Ser Lys Ser Ile Ser Pro Pro Lys Glu Lys Val Ser Phe Asp
                85                  90                  95

Asn Val Ile Asn Glu Leu Cys Thr Asp Leu Ile Leu Lys Ser Arg Gln
            100                 105                 110

Ile Lys Met Leu Ile Asp Ser Leu Pro Gly Ile Gly Val Thr Pro Asn
        115                 120                 125

Glu Gln Met Asn Leu Ile Asn Glu Leu Ser Asp Lys Leu Gln Ala Ile
130                 135                 140

Glu Glu Glu Arg Ile Gln Lys Ile Lys Glu Lys Asp Asn Leu Leu Asn
145                 150                 155                 160

Leu Leu Glu Ser Met Ile Lys Glu Val Val Asn Gly Ile Thr Glu Thr
                165                 170                 175

Arg Ile
```

<210> SEQ ID NO 3
<211> LENGTH: 140
<212> TYPE: PRT
<213> ORGANISM: Saccharomyces cerevisiae

<400> SEQUENCE: 3

```
Met Thr Asp Arg Leu Thr Gln Leu Gln Ile Cys Leu Asp Gln Met Thr
 1               5                  10                  15

Glu Gln Phe Cys Ala Thr Leu Asn Tyr Ile Asp Lys Asn His Gly Phe
            20                  25                  30

Glu Arg Leu Thr Val Asn Glu Pro Gln Met Ser Asp Lys His Ala Thr
        35                  40                  45

Val Val Pro Pro Glu Glu Phe Ser Asn Thr Ile Asp Glu Leu Ser Thr
    50                  55                  60

Asp Ile Ile Leu Lys Thr Arg Gln Ile Asn Lys Leu Ile Asp Ser Leu
65                  70                  75                  80

Pro Gly Val Asp Val Ser Ala Glu Glu Gln Leu Arg Lys Ile Asp Met
                85                  90                  95

Leu Gln Lys Lys Leu Val Glu Val Glu Asp Glu Lys Ile Glu Ala Ile
            100                 105                 110

Lys Lys Lys Glu Lys Leu Leu Arg His Val Asp Ser Leu Ile Glu Asp
        115                 120                 125
```

Phe Val Asp Gly Ile Ala Asn Ser Lys Lys Ser Thr
            130                 135                 140

<210> SEQ ID NO 4
<211> LENGTH: 144
<212> TYPE: PRT
<213> ORGANISM: Homo sapien

<400> SEQUENCE: 4

Met Ala Asp Arg Leu Thr Gln Leu Gln Asp Ala Val Asn Ser Leu Ala
 1               5                  10                  15

Asp Gln Phe Cys Asn Ala Ile Gly Val Leu Gln Gln Cys Gly Pro Pro
            20                  25                  30

Ala Ser Phe Asn Asn Ile Gln Thr Ala Ile Asn Lys Asp Gln Pro Ala
        35                  40                  45

Asn Pro Thr Glu Glu Tyr Ala Gln Leu Phe Ala Ala Leu Ile Ala Arg
    50                  55                  60

Thr Ala Lys Asp Ile Asp Val Leu Ile Asp Ser Leu Pro Ser Glu Glu
65                  70                  75                  80

Ser Thr Ala Ala Leu Gln Ala Ala Ser Leu Tyr Lys Leu Glu Glu Glu
                85                  90                  95

Asn His Glu Ala Ala Thr Cys Val Glu Asp Val Val Tyr Arg Gly Asp
            100                 105                 110

Met Leu Leu Glu Lys Ile Gln Ser Ala Leu Ala Asp Ile Ala Gln Ser
        115                 120                 125

Gln Leu Lys Thr Arg Ser Gly Thr His Ser Gln Ser Leu Pro Asp Ser
    130                 135                 140

<210> SEQ ID NO 5
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 5
ggtatagcgg ccgcgcctga tatatcaata gg                                32

<210> SEQ ID NO 6
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 6
ggttctcgag caatcgatga agaatcaagt c                                 31

<210> SEQ ID NO 7
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 7
gtcgacacag ctactagtaa ttaaggaatg ttgggttaag                        40

<210> SEQ ID NO 8
<211> LENGTH: 41
<212> TYPE: DNA

-continued

```
<213> ORGANISM: Artificial Sequence
<220> FEATURE:
<223> OTHER INFORMATION: Oligonucleotide primer

<400> SEQUENCE: 8
actagtagct gtgtcgacgg tataaccgaa acaagaatat c         41

<210> SEQ ID NO 9
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 9
gggcgcctgc agcgaacata tctacttttc a                    31

<210> SEQ ID NO 10
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 10
gggcgcagat ctgttagaga tgtggt                          26
```

CANDIDA ALBICANS SRB-7

This patent application claims priority under 35 CFR 119(e) from U.S. Provisional patent application Ser. No. 60/118,604, filed Feb. 4, 1999, which is incorporated herein by reference.

FIELD OF THE INVENTION

This invention pertains to proteins required for activated transcription in fungi, nucleic acids encoding these proteins, and methods for using these proteins.

BACKGROUND OF THE INVENTION

Most fungi are opportunistic pathogens, producing serious disease only in compromised individuals. As the result of an aging population as well as an increase in the number of immunocompromised patients, e.g., patients with acquired immunodeficiency syndrome (AIDS), patients undergoing cancer chemotherapy, or immunosuppressive therapy, e.g., treatment with corticosteroids, and patients undergoing organ transplantation, fungal infections are increasing rapidly.

Most infections begin by colonization of either the skin, a mucosal membrane, or the respiratory epithelium. Passage through the initial surface barrier is accomplished through a mechanical break in the epithelium. Although most fungi are readily killed by neutrophils, some species are resistant to phagocytic killing and can infect otherwise healthy individuals.

Fungi parasitize many different tissues. Superficial fungi cause indolent lesions of the skin. Subcutaneous pathogens cause infection through the skin and spread by subcutaneous or lymphatic routes. Opportunistic fungi such as Aspergillus are widespread in the environment and are present in normal flora. Fungi cause disease primarily in immunocompromised individuals. Systemic fungi are the most virulent and may cause progressive disease leading to deep seated visceral infections in otherwise healthy individuals (see e.g. *Sherris Medical Microbiology, Third Edition,* Kenneth J. Ryan, ed., Appleton & Lange, Norwalk, Conn., 1994).

The major fungal pathogens in North America are *Histoplasma capsulatum, Coccidioides immitis, Blastomyces dermatitidis, Cryptococcus neoformans,* Candida species, such as but not limited to *Candida albicans* and Aspergillus species (*Medically Important Fungi, Second Edition,* Davise H. Larone, Ed., American Society for Microbiology, Washington, D.C.). *C. albicans* is the most frequent cause of candidiasis; symptoms range from an acute to chronic infection involving any part of the body.

Fungi are a distinct class of microorganism, most of which are free-living. They are eukaryotic organisms containing a nuclear membrane, mitochondria and an endoplasmic reticulum. The cell structure includes a rigid cell wall of mannan, glucan, and chitin and a cytoplasmic membrane with a large percentage of ergosterol. The size and morphology of fungi vary. Candida are monomorphic yeasts and yeast-like organisms including Candida, Cryptococcus, and Saccharomyces.

Only a handful of agents are active against fungi. For life threatening disease caused by any of these fungi, amphotericin B is the agent of choice. This drug, however, is associated with numerous severe side effects such as fever, dyspnea and tachycardia, and dosage is limited over the lifetime of the patient because of renal toxicity. An agent frequently used concurrently is flucytosine, a nucleoside analog, which cannot be used independently of other agents because of the rapid appearance of resistance. Untoward effects of treatment with flucytosine include leukopenia, thrombocytopenia, rash, nausea, vomiting, diarrhea, and severe enterocolitis.

In conditions where the patient's life is not threatened, ketoconazole can be used as a long-term therapy for blastomycosis, histoplasmosis, or coccidioidomycosis. Fluconazole also has a significant role in the treatment of superficial fungal infections. Both compounds are from the same class, the triazoles, and are cytostatic. The emergence of resistance and hepatic toxicity limits the use of triazoles such as fluconazole and ketoconazole. The newest triazole, itraconazole, has similar pharmacokinetics and spectrum of activity as fluconazole. None of the azoles can be used for life threatening or deep seated fungal infections. They are only effective in reducing colonization of fungi such as Candida and for treating superficial mycoses.

All major antifungal agents attack directly or indirectly a component of the cell wall—ergosterol. Amphotericin B and other polyene macrolides interact with ergosterol in the cell membrane and form pores or channels that increase the permeability of the membrane. Resistant to amphotericin B in mutant strains is accompanied by decreased concentrations of ergosterol in their cell membranes. Imidazoles and triazoles inhibit sterol 14-α-demethylase, a microsomal cytochrome $P_{450}$-dependent enzyme system. Imidazoles and triazoles thus impair the biosythesis of ergosterol for the cytoplasmic membrane, leading to the accumulation of 14-α-methyl sterols, which impair certain membrane-bound enzyme systems (See, *The Pharmacological Basis of Therapeutics, Eighth Edition,* Goodman and Gilman, Pergamon Press, 1990).

Development of an effective method and composition for treatment of fungal infections is a critical goal of the pharmaceutical industry. The pharmaceutical industry has made numerous efforts to identify fungal-specific drugs, with only limited success to date. It would be of great value to identify a new class of antifungal drugs that block a fungal target other than ergosterol. This target should be fungal-specific and should lead to development of a drug that is effective against the organisms that are resistant to current therapy.

Drug development often relies on the screening of a large number of potential inhibitors before a specific lead compound inhibitor is found. Assays developed for such screens are complex and must mimic the physiological activity of the target protein. Thus, it is critical for the development of these screens to define the proteins involved in the targeted process and to have discovered a means of purifying the necessary components of the assay. In addition, it is useful to have clones for the protein components of the assay to facilitate the production of these fungal specific components.

Therefore, there is a need in the art to identify one or more fungal constituents, preferably polypeptides, that can serve as useful targets for drug intervention, and for methods and compositions for identifying useful anti-fungal agents and treating fungal infections.

The present invention relates to components of the transcriptional apparatus in *C. albicans.* The RNA polymerase II holoenzyme includes (i) subunits of RNA polymerase needed for some or all of the stages of transcription, but which are not specific for individual promoters and (ii) general transcription factors, termed SRBs, which bind RNA polymerase and regulate initiation of transcription at all promoters. In addition, specific transcription factors, which bind to specific sequences in particular promoters, further regulate the transcriptional activity of RNA polymerase II. All of these factors represent potential targets for antifungal agents.

SUMMARY OF THE INVENTION

Figure 2A:
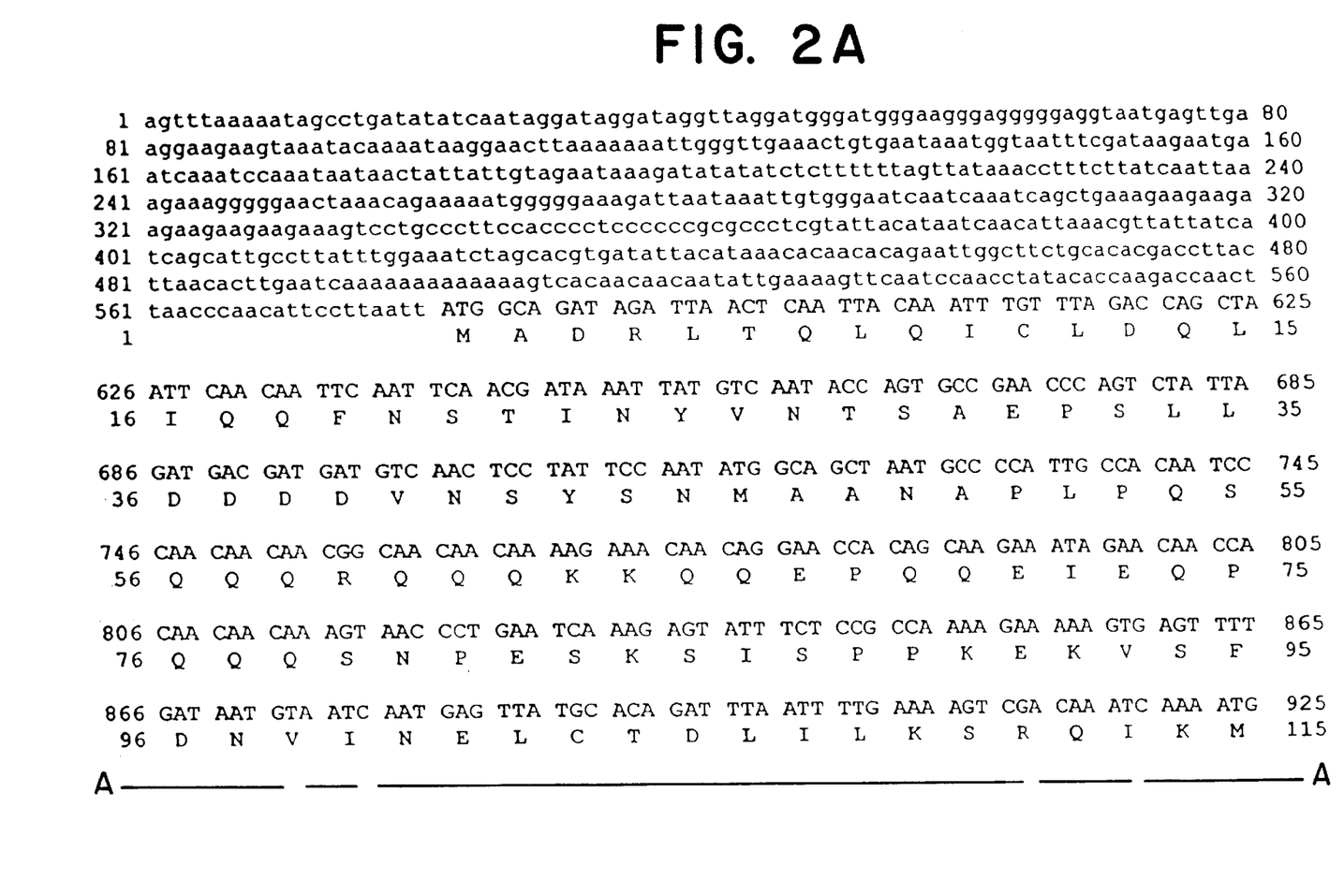
FIGS. 2A and 2B show the DNA (SEQ ID NO:1) and protein sequence (SEQ ID NO:2) of the *C. albicans* SRB-7.
Figure 2B:
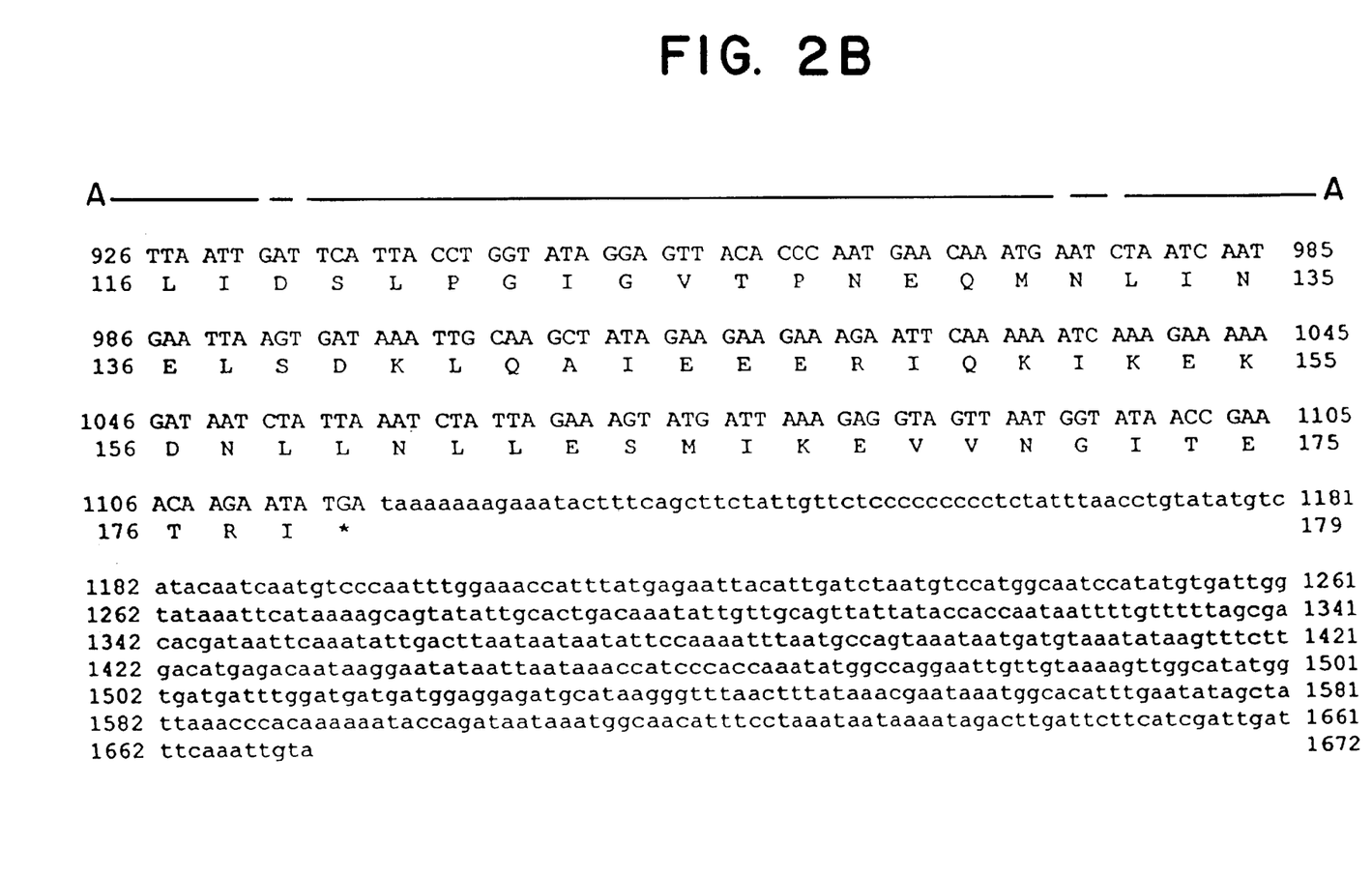

The present invention is based on the isolation of nucleic acid encoding *Candida albicans* SRB-7 (CaSRB-7), which forms part of the RNA polymerase II holoenzyme complex. In one aspect, the invention provides an isolated nucleic acid having the sequence depicted in FIG. 2, SEQ ID NO:1, as well as sequence-conservative and function-conservative variants thereof. The invention also provides vectors comprising these sequences, and cells comprising the vectors. Methods for producing the polypeptides, which comprise (i) culturing the cells and (ii) recovering the polypeptide from the culture, are also provided.

In another aspect, the invention provides an isolated polypeptide having the amino acid sequence depicted in FIG. 2, SEQ ID NO:2, and function-conservative variants thereof.

DETAILED DESCRIPTION OF THE INVENTION

All patent applications, patents, and literature references cited in this specification are hereby incorporated by reference in their entirety.

Definitions

1. "Nucleic acid" or "polynucleotide" as used herein refers to purine- and pyrimidine-containing polymers of any length, either polyribonucleotides or polydeoxyribonucleotides or mixed polyribo-polydeoxyribonucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

2. An "isolated" nucleic acid or polypeptide as used herein refers to a nucleic acid or polypeptide that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

3. A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physico-chemical properties (such as, for example, acidic, basic, hydrophobic, and the like). "Function-conservative" variants also include any polypeptides that have the ability to elicit antibodies specific to a designated polypeptide.

4. Nucleic acids are "hybridizable" to each other when at least one strand of nucleic acid can anneal to another nucleic acid strand under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarity, variables well known in the art.

In general, nucleic acid manipulations used in practicing the present invention employ methods that are well known in the art, as disclosed in, e.g., *Molecular Cloning, A Laboratory Manual* (2nd Ed., Sambrook, Fritsch and Maniatis, Cold Spring Harbor) and *Current Protocols in Molecular Biology* (Eds. Ausubel, Brent, Kingston, More, Feidman, Smith and Stuhl, Greene Publ. Assoc., Wiley-Interscience, NY, N.Y., 1997).

The present invention is based on the isolation of DNA encoding SRB-7 from *Candida albicans* (CaSRB-7). CaSRB-7 is a component of the RNA polymerase II holoenzyme and regulates the transcriptional activity of the enzyme. The discovery and characterization of CaSRB-7, and the elucidation of differences between the fungal and mammalian versions, implicates this protein as an important target for the development of new methods and compositions for the treatment of fungal infections. As shown in Example 1 below, deletion analysis demonstrated that SRB-7 was essential for cell viability. Therefore, agents which selectively interfere with CaSRB-7 activity would likely be candidates for anti-*C. albicans* therapeutics. The present invention also encompasses methods for identifying compounds that selectively interfere with CaSRB-7 activity and thus may comprise useful antifungal agents.

The gene encoding CaSRB-7 was isolated as follows (see, Example 1 below). Briefly, a genomic library from *C. albicans* was used to transform a strain of *S. cerevisiae* lacking a functional SRB-7 gene. A *C. albicans*-derived DNA fragment capable of complementing the SRB-7-deficient phenotype was identified and isolated. Nucleotide sequencing of the DNA identified by this procedure (FIG. 2) revealed an open reading frame of 534 bp encoding a protein of 178 amino acids which shows significant homology to SRB-7 polypeptides from *S. cerevisiae* and humans. Notably, however, the inferred amino acid sequence of CaSRB-7 diverges considerably from that of *S. cerevisae* and humans. *C. albicans* and *S. cerevisiae* are 45% identical over the full length proteins while the two fungal species display approximately 25% sequence homology with human SRB-7.

The present invention provides isolated nucleic acids encoding CaSRB-7, such as, e.g., the nucleic acid sequence depicted in FIG. 2 (SEQ ID NO:1). The invention also encompasses isolated nucleic acids encoding enzymatically active fragments derived therefrom, and related sequences. As used herein, a nucleic acid that is "derived from" a sequence refers to a nucleic acid sequence that corresponds to a region of the sequence, sequences that are homologous or complementary to the sequence, sequence-conservative variants, and function-conservative variants. Important regions of CaSRB-7 can be identified by employing the technique used to clone the gene, i.e., functional complementations in *S. cerevisiae*. Point mutations and deletions can be made in the CaSRB-7 gene, using techniques well known to those of ordinary skill in the art, and it can be determined if these mutant genes will functionally substitute for *S. cerevisiae* SRB-7 using e.g., plasmid shuffle techniques described hereinbelow in Example 1.

Also encompassed by the invention are nucleic acids that are hybridizable to, or derived from, the CaSRB-7 sequences described above. In one embodiment, the invention relates to isolated nucleic acids capable of hybridizing with the CaSRB-7 sequences or with their complements under the hybridization conditions defined below.

- Prehybridization treatment of the support (nitrocellulose filter or nylon membrane), to which is bound the nucleic acid capable of hybridizing with nucleic acid encoding CaSRB-7 at 65° C. for 6 hours with a solution having the following composition: 4×SSC, 10×Denhardt (1X Denhardt is 1% Ficoll, 1% polyvinylpyrrolidone, 1% BSA (bovine serum albumin); 1×SSC consists of 0.15M of NaCl and 0.015M of sodium citrate, pH 7);
- Replacement of the pre-hybridization solution in contact with the support by a buffer solution having the following composition: 4×SSC, 1×Denhardt, 25 mM NaPO$_4$, pH 7, 2 mM EDTA, 0.5% SDS, 100 μg/ml of sonicated salmon sperm DNA containing a nucleic acid derived from the CaSRB-7 sequence as probe, in particular as radioactive probe, and previously denatured by a treatment at 100° C. for 3 minutes;
- Incubation for 12 hours at 65° C.;
- Successive washings with the following solutions: (i) four washings with 2×SSC, 1×Denhardt, 0.5% SDS for 45 minutes at 65° C.; (ii) two washings with 0.2×SSC, 0.1×SSC for 45 minutes at 65° C.; and (iii) 0.1×SSC, 0.1% SDS for 45 minutes at 65° C.

The invention also encompasses any nucleic acid exhibiting the property of hybridizing specifically with the above-described CaSRB-7-encoding DNA under the conditions described above, but at 40° C., including successive washings in 2X SSC at 45° C. for 15 minutes.

It will be understood that the conditions of hybridization defined above constitute preferred conditions for the hybridization, but are in no way limiting and may be modified without in any way affecting the properties of recognition and hybridization of the probes and nucleic acids mentioned above.

The salt conditions and temperature during the hybridization and the washing of the membranes can be modified in the sense of a greater or lesser stringency without the detection of the hybridization being affected. For example, it is possible to add formamide in order to lower the temperature during hybridization.

The invention also encompasses vectors comprising CaSRB-7-encoding sequences, cells comprising the vectors, and methods for producing CaSRB-7 that involve culturing the cells.

A large number of vectors, including plasmid and fungal vectors, have been described for expression in a variety of eukaryotic and prokaryotic hosts. Advantageously, vectors may also include a promotor operably linked to the CaSRB-7 encoding portion. The encoded CaSRB-7 may be expressed by using any suitable vectors and host cells, using methods disclosed or cited herein or otherwise known to those skilled in the relevant art. The particular choice of vector/host is not critical to the invention.

Vectors will often include one or more replication systems for cloning or expression, one or more markers for selection in the host, e.g. antibiotic resistance, and one or more expression cassettes. The inserted CaSRB-7 coding sequences may be synthesized, isolated from natural sources, prepared as hybrids, etc. Ligation of the coding sequences to the transcriptional regulatory sequences may be achieved by known methods. Suitable host cells may be transformed/transfected/infected by any suitable method including electroporation, CaCl$_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *E. coli*, *B. subtilis*, *S. cerevisiae*, SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under the appropriate expression conditions, host cells can be used as a source of recombinantly produced CaSRB-7.

Nucleic acids encoding wild-type or variant CaSRB-7 polypeptides may also be introduced into cells by recombination events. For example, such a sequence can be introduced into a cell, and thereby effect homologous recombination at the site of an endogenous gene or a sequence with substantial identity to the gene. Other recombination-based methods, such as non-homologous recombinations or deletion of endogenous genes by homologous recombination, may also be used.

The invention also encompasses isolated and purified CaSRB-7 polypeptides, including, e.g., a polypeptide having the amino acid sequence depicted in FIG. 2 (SEQ ID NO:2), as well as function-conservative variants of this polypeptide, including fragments that retain transcriptional regulatory activity as described above.

CaSRB-7-derived polypeptides according to the present invention, including function-conservative variants, may be isolated from wild-type or mutant *C. albicans* cells, or from heterologous organisms or cells (including, but not limited to, bacteria, fungi, insect, plant, and mammalian cells) into which a CaSRB-7-derived protein-coding sequence has been introduced and expressed. Furthermore, the polypeptides may be part of recombinant fusion proteins.

Alternatively, polypeptides may be chemically synthesized by commercially available automated procedures, including, without limitation, exclusive solid phase synthesis, partial solid phase methods, fragment condensation or classical solution synthesis.

"Purified" CaSRB-7 polypeptides can be obtained by using conventional techniques. Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against CaSRB-7 or against peptides derived therefrom can be used as purification reagents. Other purification methods are possible.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The present invention encompasses antibodies that are specific for CaSRB-7 or fragment identified as described above. As used herein, antibodies "specific" for CaSRB-7 include without limitation antibodies that: distinguish CaSRB-7 from other nuclear proteins, discriminate CaSRB-7 from different species, identify associational or other functional domains, and the like. The antibodies may be polyclonal or monoclonal. The antibodies may be elicited in an animal host by immunization with CaSRB-7 or fragments derived therefrom or may be formed by in vitro immunization of immune cells. The immunogens used to elicit the antibodies may be isolated from *C. albicans* cells or produced in recombinant systems. The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and $F(ab)_2$ fragments of antibodies.

Methods for the production of all of the above types of antibodies and derivatives are well-known in the art and are discussed in more detail below. For example, techniques for producing and processing polyclonal antisera are disclosed in Mayer and Walker, 1987, *Immunochemical Methods in Cell and Molecular Biology*, (Academic Press, London). Such antibodies are conveniently made using the methods and compositions disclosed in Harlow and Lane, *Antibodies, A Laboratory Manual*, Cold Spring Harbor Laboratory, 1988, as well as immunological and hybridoma technologies known to those of ordinary skill in the art. Where natural or synthetic CaSRB-7-derived peptides are used to induce an CaSRB-7-specific immune response, the peptides may be conveniently coupled to a suitable carrier such as KLH and administered in a suitable adjuvant such as Freunds. Preferably, selected peptides are coupled to a lysine core carrier substantially according to the methods of Tam (*Proc Natl Acad Sci USA* 85:5409, 1988).

In one embodiment, purified recombinant CaSRB-7 is used to immunize mice, after which their spleens are removed, and splenocytes used to form cell hybrids with myeloma cells and obtain clones of antibody-secreted cells according to techniques that are standard in the art. The resulting monoclonal antibodies are screened using in vitro assays such as those described above for binding to CaSRB-7 or inhibition of the incorporation of CaSRB-7 into RNA holoenzyme type II.

Anti-CaSRB-7 antibodies may be used to quantify CaSRB-7, using immunoassays such as, but not limited to ELISA. Anti-CaSRB-7 antibodies may also be used to block the transcriptional function of RNA polymerase II by inhibiting the formation of complexes between CaSRB-7 subunits or between assembled RNA polymerase II complexes and other transcription components, or by immunodepleting cell extracts or transcription reactions of CaSRB-7. In addition, these antibodies can be used to identify, isolate, and purify CaSRB-7 from different sources, and to perform subcellular and histochemical localization studies.

Methods for Modifying Transcription

The present invention provides methods of modifying gene transcription by substances that bind to, or interact with the CaSRB-7 protein or the DNA/RNA encoding the CaSRB-7 protein. These substances modify the influence of the CaSRB-7 protein on RNA polymerase II, or on other transcription factors essential to gene transcription. Substances that bind to, or interact with the CaSRB-7 protein or the DNA/RNA encoding the CaSRB-7 protein can prevent or enhance the formation of the RNA polymerase II holoenzyme complex, thus inhibiting or enhancing gene transcription. For example, antisense or nonsense nucleotide sequences that hybridize with the CaSRB-7 DNA or RNA and completely inhibit, or decrease their translation or transcription can prevent the formation of the holoenzyme complex and inhibit gene transcription. Alternatively, even though the holoenzyme complex is formed, substances that can bind to or interact with the CaSRB-7 protein can prevent or enhance the function of the complex in the transcription process. These substances include antibodies that are reactive with and bind to the CaSRB-7 protein.

High-Throughput Drug Screening

The present invention encompasses the identification of agents useful in modulating fungal gene transcription, particularly the transcription of genes by RNA polymerase II in a CaSRB-7-dependent manner. In a preferred embodiment, a high-throughput screening protocol is used to survey a large number of test compounds for their ability to interfere with CaSRB-7-dependent processes.

Test inhibitory compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through conventional chemical, physical, and biochemical means.

Useful inhibitory agents may identified using assays that employ CaSRB-7 encoding nucleic acids. As examples, protein binding assays, nucleic acid binding assays and gel shift assays are useful approaches. Preferably, RNA polymerase II complexes or subunits (Kim et al., 1994; Hengartner et al., 1995) may be used in in vitro binding assays with either CaSRB-7 alone or with a combination or sub-combination of CaSRB-7 as well as other general transcription factors, e.g., SRB-2, 4,5, 6, 8, 9, 10, 11, etc.

For example, RNA polymerase II complexes or subunits may be immobilized on microtiter dishes using methods that are standard in the art. The plates are then exposed to radiolabelled CaSRB-7 e.g. $^{32}$P-CaSRB-7 in the absence or presence of candidate compounds. Conversely, CaSRB-7 may be immobilized, and incubated with radiolabelled RNA polymerase II in the absence or presence of candidate compounds. Oligonucleotides comprising CaSRB-7 target sequences may be used in conjunction with RNA polymerase II. Positive "hit" compounds are those that inhibit CaSRB-7/RNA polymerase II interaction. In these case, incubation, washing, and radioactivity detection steps can be automated, allowing the screening of a large number of compounds, preferably at least about 1000 compounds per week.

High-throughput screening methods described in U.S. Pat. Nos. 5,585,277 and 5,679,582, in U.S. Ser. No. 08/547, 889, and in PCT published application PCT/US96/19698 may be used for identifying a ligand that binds the CaSRB-7 protein. According to these methods, a ligand, or a plurality of ligands for CaSRB-7 target protein is identified by its ability to influence the extent of folding or the rate of folding or unfolding of the target protein. Experimental conditions are chosen so that the target protein is subjected to unfolding, whether reversible or irreversible. If the test ligand binds to the target protein under these conditions, the relative amount of folded:unfolded target protein or the rate of folding or unfolding of the target protein in the presence of the test ligand will be different, i.e. higher or lower, than that observed in the absence of the test ligand. Thus, the method encompasses incubating CaSRB-7 in the presence and absence of a test ligand or ligands, under conditions in which (in the absence of ligand) the CaSRB-7 protein would partially or totally unfold. This is followed by analysis of the absolute or relative amounts of folded vs. unfolded target protein or of the rate of folding or unfolding of the target protein.

An important feature of this method is that it will detect any compound that binds to any sequence or domain of the CaSRB-7, and not only to sequences or domains that are intimately involved in a biological activity or function. The binding sequence, region, or domain may be present on the surface of the CaSRB-7 when it is in its folded state, or may be buried in the interior of the protein. Some binding sites may only become accessible to ligand binding when the protein is partially or totally unfolded.

Briefly, to carry out this method, the test ligand or ligands are combined with the CaSRB-7, and the mixture is maintained under appropriate conditions and for a sufficient time to allow binding of the test ligand. Experimental conditions are determined empirically. When testing test ligands, incubation conditions are chosen so that most ligand:CaSRB-7 protein interactions would be expected to proceed to completion. The test ligand is present in molar excess relative to the CaSRB-7. The target protein can be in a soluble form, or, alternatively, can be bound to a solid phase matrix. The matrix may comprise without limitation beads, membrane filters, plastic surfaces, or other suitable solid supports.

In a preferred embodiment, binding of test ligand or ligands to CaSRB-7 is detected through the use of proteolysis. This assay is based on the increased susceptibility of unfolded, denatured polypeptides to protease digestion relative to that of folded proteins. In this case, the test ligand-CaSRB-7 protein combination, and a control combination lacking the test ligand, are treated with one or more proteases that act preferentially upon unfolded target protein. After an appropriate period of incubation, the level of intact i.e. unproteolysed target protein is assessed using one of the methods described below e.g. gel electrophoresis and/or immunoassay.

There are two possible outcomes that indicate that the test ligand has bound the target protein. Either 1) a significantly higher, or 2) a significantly lower, absolute amount of intact or degraded protein may be observed in the presence of ligand than in its absence.

Proteases useful in practicing the present invention include without limitation trypsin, chymotrypsin, V8 protease, elastase, carboxypeptidase, proteinase K, thermolysin, papain and subtilisin (all of which can be obtained from Sigma Chemical Co., St. Louis, Mo.). The most important criterion in selecting a protease or proteases for use in practicing the present invention is that the protease (s) must be capable of digesting the CaSRB-7 protein under the chosen incubation conditions, and that this activity be preferentially directed towards the unfolded form of the protein. To avoid "false positive" results caused by test ligands that directly inhibit the protease, more than one protease, particularly proteases with different enzymatic mechanisms of action, can be used simultaneously or in parallel assays. In addition, co-factors that are required for the activity of the protease(s) are provided in excess, to avoid false positive results due to test ligands that may sequester these factors.

In a typical embodiment of this method, purified CaSRB-7 protein is first taken up to a final concentration of 1–100 μg/ml in a buffer containing 50 mM Tris-HCl, pH 7.5, 10% DMSO, 50 mM NaCl, 10% glycerol, and 1.0 mM DTT. Proteases, such as, for example, proteinase K or thermolysin (proteases with distinct mechanisms of action), are then added individually to a final concentration of 0.2–10.0 μg/ml. Parallel incubations are performed for different time periods ranging from 5 minutes to one hour, preferably 30 minutes, at 4° C., 15 ° C., 25 ° C., and 35° C. Reactions are terminated by addition of an appropriate protease inhibitor, such as, for example, phenylmethylsulfonyl chloride (PMSF) to a final concentration of 1 mM (for serine proteases), ethylenediaminotetraacetic acid (EDTA) to a final concentration of 20 mM (for metalloproteases), or iodoacetamide (for cysteine proteases). The amount of intact protein remaining in the reaction mixture at the end of the incubation period may then be assessed by any method, including without limitation polyacrylamide gel electrophoresis, ELISA, or binding to nitrocellulose filters. It will be understood that additional experiments employing a narrower range of temperatures can be performed to establish appropriate conditions. This protocol allows the selection of appropriate conditions (e.g., protease concentration and digestion temperature) that result in digestion of approximately 70% of the target protein within a 30 minute incubation period, indicating that a significant degree of unfolding has occurred.

In another embodiment, the relative amount of folded and unfolded CaSRB-7 protein in the presence and absence of test ligand is assessed by measuring the relative amount of the protein that binds to an appropriate surface. This method takes advantage of the increased propensity of unfolded proteins to adhere to surfaces, which is due to the increased surface area, and decrease in masking of hydrophobic residues, that results from unfolding. If a test ligand binds the CaSRB-7 (i.e., is a ligand), it may stabilize the folded form of the target protein and decrease its binding to a solid surface. Alternatively, a ligand may stabilize the unfolded form of the protein and increase its binding to a solid surface.

Surfaces suitable for this purpose include without limitation microtiter plates constructed from a variety of treated or untreated plastics, plates treated for tissue culture or for high protein binding, nitrocellulose filters and PVDF filters.

In another embodiment, the extent to which folded and unfolded target protein are present in the test combination is assessed through the use of antibodies specific for either the unfolded state or the folded state of the protein i.e. denatured-specific ("DS"), or native-specific ("NS") antibodies, respectively. (Breyer, 1989, *J. Biol. Chem.,* 264 (5):13348–13354). Polyclonal or monoclonal antibodies are prepared as described above. The resulting antibodies are screened for preferential binding to the CaSRB-7 protein in its denatured state. These antibodies are used to screen for inhibitors of these interactions.

In another embodiment, molecular chaperones are used to assess the relative levels of folded and unfolded protein in a test combination. Chaperones encompass known proteins that bind unfolded proteins as part of their normal physiological function. In this embodiment, a test combination containing the test ligand and the CaSRB-7 is exposed to a solid support e.g. microtiter plate or other suitable surface coated with a molecular chaperone, under conditions appropriate for binding the CaSRB-7 with its ligand and binding of the molecular chaperone to unfolded target protein. The unfolded target protein in the solution will have a greater tendency to bind to the molecular chaperone-covered surface relative to the ligand-stabilized folded target protein. Thus, the ability of the test ligand to bind target protein can be determined by determining the amount of target protein remaining unbound, or the amount bound to the chaperone-coated surface. Alternatively, a competition assay for binding to molecular chaperones can be utilized.

Once conditions are established for high-throughput screening as described above, the protocol is repeated simultaneously with a large number of test ligands at concentrations ranging from 20 to 200 $\mu$M. Observation of at least a two-fold increase or decrease in the extent of digestion of the target protein signifies a "hit" compound, i.e., a ligand that binds the target protein. Preferred conditions are those in which between 0.1% and 1% of test ligands are identified as "hit" compounds using this procedure.

In yet another embodiment, the test and control combinations described above can be contacted with a conformation-sensitive fluorescence probe, i.e., a probe that binds preferentially to the folded, unfolded, or molten globule state of the CaSRB-7 or whose fluorescence properties are in any way affected by the folding status of the CaSRB-7 protein.

Once a particular test compound has been identified as described above, its activity is confirmed by adding it to an in vitro transcription reaction, and measuring its effect on CaSRB-7-mediated activated transcription, using an in vitro transcription assay. For example, DNA of interest (i.e., DNA to be transcribed) can be admixed with (i) purified RNA polymerase II, (ii) the SRB proteins, (iii) transcription factors b, e, g or a (Koleske and Young, *Nature* 368:466–469, 1994), (iv) CaSRB-7 and (v) the substance to be tested. The mixture is maintained under conditions sufficient for transcription to occur. The resulting combination is referred to as a test mixture. DNA transcription can be assessed by determining the quantity of mRNA produced. Transcription is determined in the presence of the substance being tested and compared to DNA transcription in the absence of the test substance taking place under identical conditions (e.g., a control mixture). If transcription occurs to a lesser extent in the test mixture, (i.e., in the presence of the substance being evaluated) than in the control mixture, the substance has interacted with one, or more SRB proteins, preferably CaSRB-7, in such a manner as to inhibit transcription. If transcription occurs to a greater extent in the test mixture than in the control mixture, the substance has interacted with one or more SRB proteins, preferably CaSRB-7, in such a manner as to stimulate transcription.

Transcription of DNA sequences, or translation of mRNA sequences encoding the CaSRB-7 protein can also be inhibited or decreased, resulting in decreased production of, or complete absence of CaSRB-7. Gene transcription can be modified by introducing an effective amount of a substance into a cell that inhibits transcription of the CaSRB-7 gene, or that inhibits translation of mRNA encoding the CaSRB-7 gene product. For example, antisense nucleotide sequences can be introduced into the cell that will hybridize with the gene encoding the CaSRB-7 protein and inhibit transcription of the gene. (See, *Current Protocols in Molecular Biology,* Eds. Ausubel et al. Greene Publ. Assoc., Wiley-Interscience, NY, N.Y., 1997). Alternatively, an antisense sequence can be introduced into the cell that will interfere with translation of the mRNA encoding a CaSRB-7 protein.

In addition, a test compound identified as described above is tested for two properties: 1) its ability to inhibit fungal growth; and 2) its lack of effect on mammalian transcription. Fungal growth is measured by any method well-known in the art e.g. optical density of a liquid culture, or colony formation on agar. The lack of effect of a test compound on mammalian SRB-7-RNA polymerase II interaction is tested by replacing yeast components with an analogous human in vitro transcription system as in Chao et al., 1996.

Additional transcription assays useful for identifying test compounds are disclosed in PCT Publication No. WO 97/09301.

The following examples are intended as non-limiting illustration of the present invention.

EXAMPLE 1

Isolation and Sequencing of DNA Encoding *Candida Albicans* SRB-7

The following experiments were performed to identify DNA derived from *C. albicans* that encodes SRB-7.

DNA Methods and Genetic Manipulations

Yeast strains, plasmids, and oligonucleotides are listed in tables one, two, and three, respectively. All DNA manipulations were performed according to Sambrook et al. (1989). Yeast medium was prepared as described (Guthrie and Fink, 1991). *Saccharomyces cerevisiae* transformations were done using a lithium acetate procedure (Schiestl and Gietz, 1989). *Candida albicans* transformations were performed as described (Elble, 1992). Plasmid shuffle techniques were performed as described (Boeke et al., 1987) using 5-flouro-orotic acid (5-FOA) as a selective agent against URA3 plasmids.

A *C. albicans* genomic library was prepared from strain SC5314 (Fonzi and Irwin, 1993). Genomic DNA was isolated as described by Phillippsen et al. (1991), partially digested with Sau3A, separated on a 0.7% agarose gel, 4–8 kb fragments purified by GeneClean (BIO101, La Jolla, Calif.), and the ends partially filled in with d(AG) TP using Klenow. A LEU2, 2 micron plasmid (pCT538) was digested with XhoI, and the ends partially filled in with d(CT)TP to make them compatible with the ends of the Sau3A-digested genomic DNA. Following ligation, SURE cells (Stratagene, La Jolla, Calif.) were transformed by electroporation. Approximately 25,000 individual clones were obtained with a 90% insert efficiency and 5 kb average insert size.

DNA sequencing reactions were performed with Taq DNA polymerase and a thermocycler and run on a ABI sequencing gel. Sequence alignments were done with the Lasergene software package from DNASTAR Inc (Madison, Wis.).

Cloning and Sequence Analysis of C. albicans SRB-7

A full-length *Candida albicans* SRB-7 homolog was isolated by functional complementation of a *S. cerevisiae* SRB-7 deletion mutant (Z704) using a plasmid shuffle technique. Z704 (Chao et al., 1996) cells were transformed with a *C. albicans* SC5314 genomic DNA library constructed in a *S. cerevisiae* LEU2 2 micron plasmid (pCT538). Transformed cells were grown in liquid media lacking leucine for 12 hours to permit loss of the ScSRB-7 URA3 plasmid, then placed on agar media lacking leucine and containing 5-FOA. Ten *C. albicans* genomic clones with overlapping restriction enzyme fragments were isolated from Leu+transformants able to grow in the presence of 5-FOA. The clone with the smallest genomic DNA insert (pCT568) was selected for further analysis.

Figure 1:
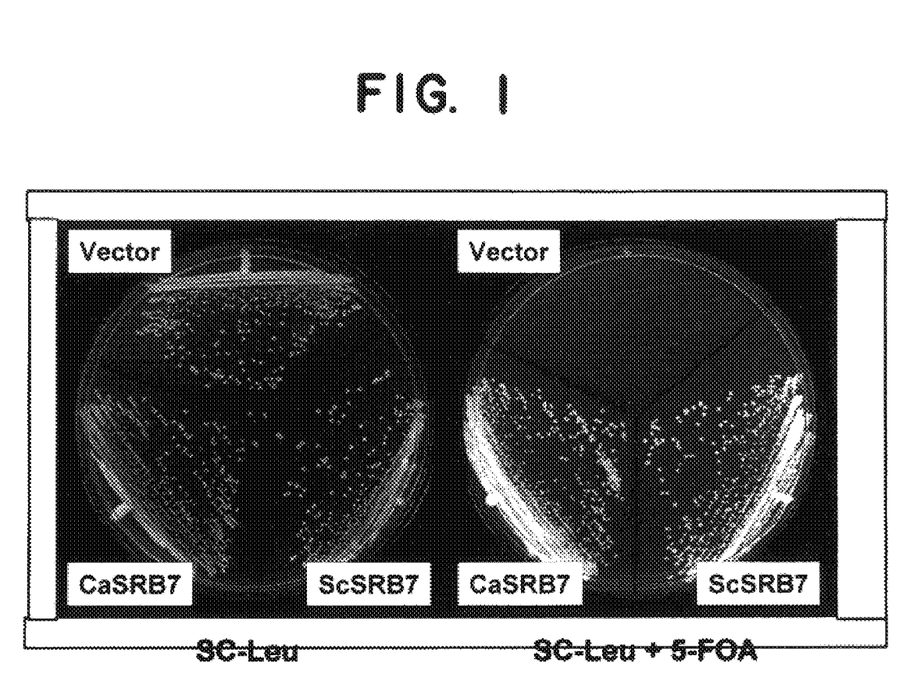
FIG. 1 shows the result of a plasmid shuffle technique using 5-fluoro-orotic acid (5-FOA) as a selective agent against URA 3 plasmids. *S. cerevisiae,* with a SRB-7 deletion were placed on agar media lacking leucine, selecting for the transformed LEU 2 marked plasmids, either in the absence (FIG. 1A) or presence of 5-FOA (FIG. 1B).

To confirm the ability of pCT568 to substitute for *S. cerevisiae* SRB-7, Z704 was transformed with pCT538 (vector only), pCH50 (ScSRB-7), and pCT568 (CaSRB-7), respectively. Cells were placed on agar media lacking leucine, selecting for the transformed LEU2 marked plasmids, either in the absence (FIG. 1A) or presence of 5-FOA (FIG. 1B). All three cell types grew equally well in the absence of 5-FOA. When the URA3 ScSRB-7 containing plasmid was selected against by the presence of 5-FOA, cells transformed by ScSRB-7 or CaSRB-7 on a LEU2 plasmid grew equally well while those cells transformed by the vector alone failed to grow. This experiment confirmed that pCT568 contains a *C. albicans* gene that will complement a *S. cerevisiae* SRB-7 deletion.

Figure 3:
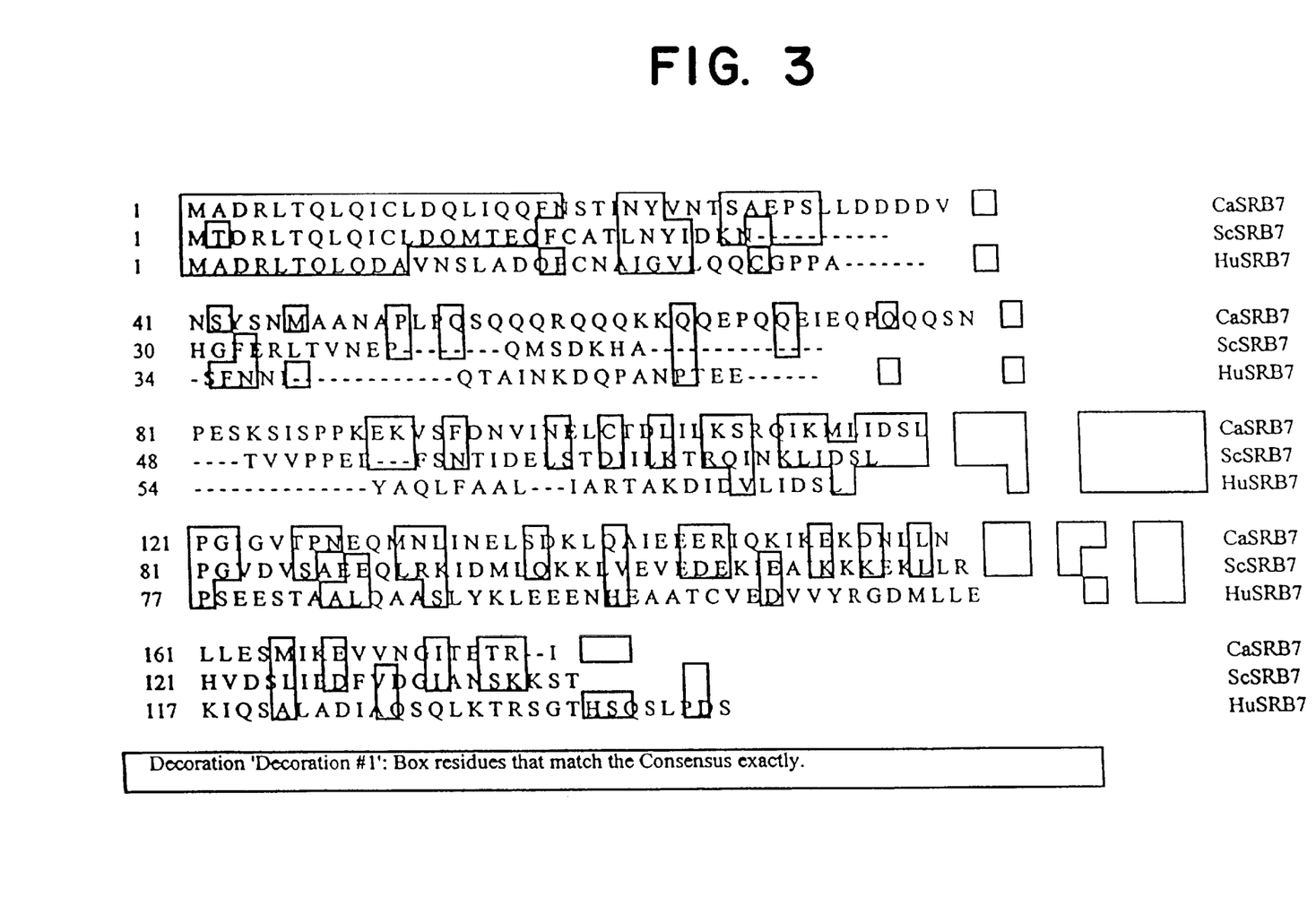
FIG. 3 shows the sequence identity between the *C. albicans* (SEQ ID NO:3), *S. cerevisiae* and human (SEQ ID NO:4) SRB-7 protein sequences.

The 4.3 kb genomic insert from pCT568 was completely sequenced and a 534 bp open reading frame was identified that predicts a protein of 178 amino acids (FIG. 2) with significant sequence identity to *S. cerevisiae* (SEQ ID NO:3) and human (SEQ ID NO:4) SRB-7 (FIG. 3). *C. albicans* (SEQ ID NO:2) and *S. cerevisiae* (SEQ ID NO:3) SRB-7 are 45% identical over the full-length proteins while the two fungal species display approximately 25% sequence identity with human SRB-7.

Deletion Analysis of C. albicans SRB-7

Deletion analysis of *C. albicans* SRB-7 was used to establish that CaSRB-7 is essential for cell viability. Plasmid pCT578 (Δcasrb7) was created by two-step PCR. In the first round of synthesis, oligos CaSRB-7p15 (forward direction, approximately 570 nucleotides upstream of the ATG) (SEQ ID NO:5) and CaSRB-7p20 (reverse direction, immediately upstream of ATG) (SEQ ID NO:7) were used to create a fragment containing the CaSRB-7 5' (SEQ ID NO:7) flanking region that included a NotI and SpeI site at the 5' and 3' ends, respectively. Oligos CaSRB-7p21 (SEQ ID NO:8) (forward direction, immediately 3' of the ORF) and CaSRB-7p19 (reverse direction, 500 nucleotides downstream of the SRB-7 stop codon) (SEQ ID NO:6) were used to create a 3' flanking region that was framed by SalI and XhoI sites at the 5' and 3' end, respectively. The two products were combined with primers CaSRB-7p15 (SEQ ID NO:5) and CaSRB-7p19 (SEQ ID NO:6) to amplify a 1.1 Kb_CaSRB-7 fragment that was digested with NotI and XhoI and inserted into pBSIISK(+) (Stratagene, La Jolla, Calif.). pCT568, a *C. albicans* SRB-7 clone isolated by complementation of an *S. cerevisiae* deletion, was used as template for the PCR reactions.

Plasmid pCT580 (Δcasrb7::CaURA3) was created by insertion of a 1.4 Kb SalI-SpeI CaURA3 fragment from pCT570 into SalI-SpeI of pCT578. Plasmid pCT570 was created by inserting a 1.4 Kb HindIII-BamHI fragment containing CaURA3 from pDBV51 (Brown et al., 1996) into HindIII-BamHI of pBSIISK(+) (Stratagene, La Jolla, Calif.).

Plasmid pSH209 (CaADE2) was created by first PCR amplifying a 2.2 Kb CaADE2 fragment from genomic DNA from strain SC5314 of *C. albicans* (Fonzi and Irwin, 1993). The primers used, pCaADE2f (SEQ ID NO:9) and pCaADE2b, (SEQ ID NO:10) included a PstI and BglII site, respectively. The PCR product was digested with PstI and BglII and inserted into PstI-BamHI of pRS315 (Sikorski and Hieter, 1989). Plasmid pSH210 (Δcasrb7::ADE2) was created by insertion of the 2.2 Kb SalI-SpeI CaADE2 fragment from pSH209 into SalI-SpeI of pCT578.

To create a single disruption of SRB-7 in *C. albicans* strain CAI8 (Fonzi and Irwin, 1993), cells were transformed with plasmid pSH210 (Δcasrb7::ADE2) that had been digested with NotI/XhoI and ADE+prototrophs were selected. Integration of the Δcasrb7::ADE2 cassette at SRB-7 was verified by Southern using a probe containing the CaSRB-7 5' flanking region. Four of 4 Ade+ transformants showed the expected 4.2 Kb NcoI/SnaBIΔcasrb7::ADE2 band in addition to the wildtype non-disrupted band 2.6 Kb (data not shown). One of these singly disrupted strains (SHC1) was selected for further analysis.

Figure 4:
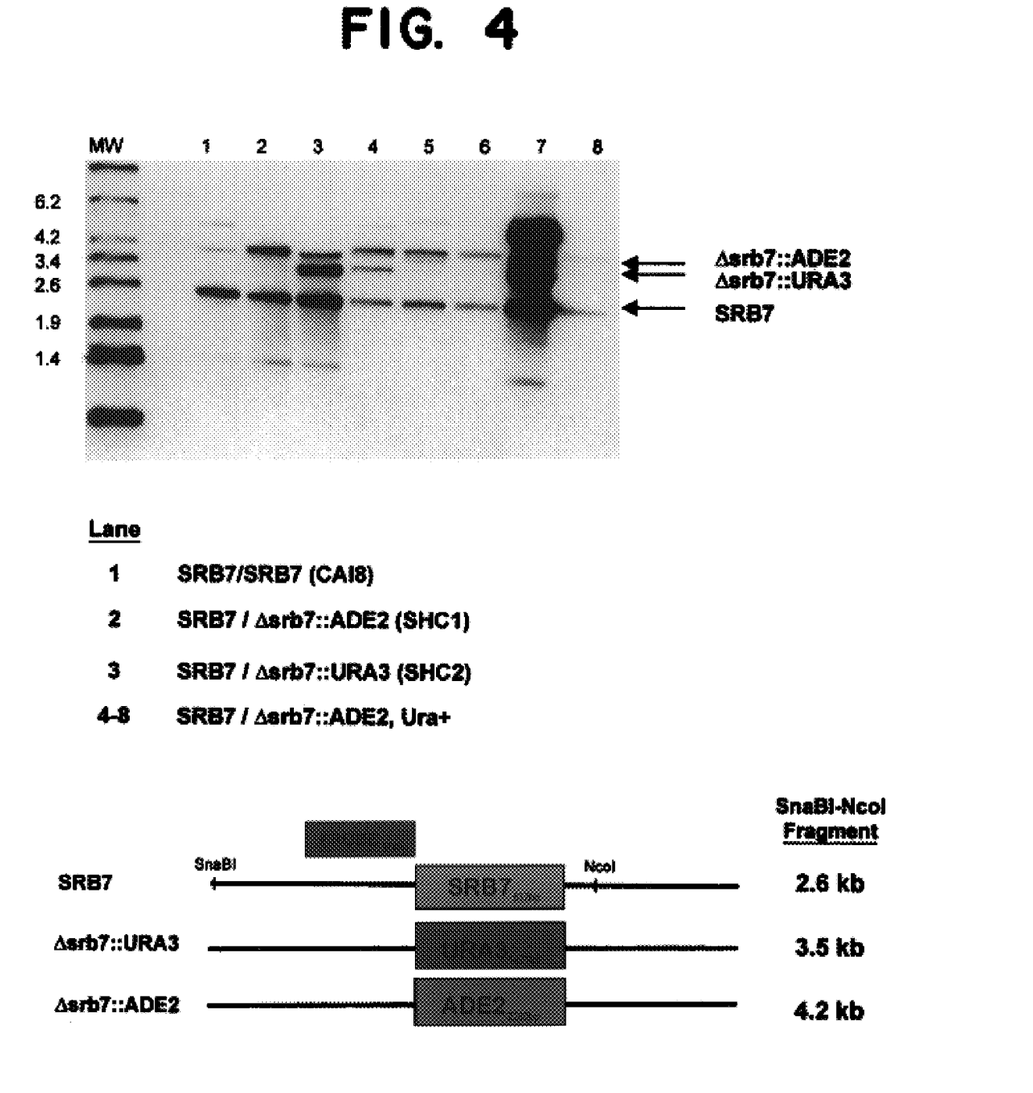
FIG. 4 displays the results of a Southern blot analysis showing that SRB-7 is essential for cell viability.

An attempt was then made to delete the second SRB-7 allele. The singly disrupted strain SHC1 (SRB-7/casrb7::ADE2) was transformed with pCT580 (Δcasrb7::URA3) that had been digested with NotI/XhoI and Ade+Ura+ transformants were selected. Ura+Ade+ transformants were screened by Southern blot using the SRB-7 5' probe described above. Deletion of the second copy of SRB-7 should result in a new 3.5 Kb NcoI/SnaBIΔcasrb7::URA3 fragment and the disappearance of the 2.6 kb wildtype band. However, in 20 of 20 transformants, the 2.6 Kb wildtype band was still present, indicating that it was not possible to delete the second allele and strongly suggesting that SRB-7 is essential for cell viability. FIG. 4 displays the results of this Southern blot analysis for 5 of the 20 transformations. As a control, CAI8 was transformed with NotI/XhoI digested pCT580 (Δcasrb7::URA3) and Ura+ transformants selected. Analysis of one of these transformants (SCH2) is shown in FIG. 4.

TABLE 1

Yeast Strains

| Strain | Genotype | Source or Reference |
|---|---|---|
| *Saccharomyces cerevisiae* | | |
| Z704 | Mata his3Δ200 leu2-3, 112 ura3-52 srb7Δ1::hisG pCH7(ScSRB7,URA3,CEN) | Chao et al, 1996 |
| CTY557 | Mata his3Δ200 leu2-3, 112 ura3-52 srb7Δ1::hisG pCH5O(ScSRB7,LEU2,CEN) | Craig Thompson[1] |

TABLE 1-continued

Yeast Strains

| Strain | Genotype | Source or Reference |
|---|---|---|
| CTY560 | Mata his3Δ200 leu2-3, 112 ura3-52 stb7Δ1::hisG pCT568 (CaSRB7, LEU2, 2 micron | Craig Thompson[1] |
| *Candida albicans* | | |
| CAI8 | ade2::hisG-URA-3-hisG/ade2::hisG Δura3::imm434/Δura3::imm434 | Fonziand Irwin 1993 |
| SHC1 | ade2::hisG-URA3-hisG/ade2::hisG Δura3::imm434/Δura3::imm434 SRB7/ Δsrb7::ADE2 | Sandra Harris[1] |
| SHC2 | ade2::hisG-URA3-his.G/ade2::hisG Δura3::imm434/Δura3::imm434 SRB7/Δsrb7::URA3 | Sandra Harris[1] |

[1]Unpublished
Scriptgen Pharmaceuticals, Waltham, MA 02451

TABLE 2

Plasmids

| Plasmid | Description | Source |
|---|---|---|
| pCH7 | *S. cerevisiae* SRB7, URA3, CEN | Rick Young[1] |
| pCH50 | *S. cerevisae* SRB7, LEU2, CEN | Rick Young[2] |
| pCT558 | LEU2, 2 micron | Craig Thompson[3] |
| pCT568 | *C. albicans* SRB7, LEU2, 2 micron | Craig Thompson[3] |
| pCT570 | *C. albicans* URA3 | Craig Thompson[3] |
| pCT578 | Δ*C. albicans* srb7 | Craig Thompson[3] |
| pCT580 | Δ*C. albicans* srb7::*C. albicans* URA3 | Craig Thompson[3] |
| pSH209 | *C. albicans* ADE2 | Sandra Harris[3] |
| pSH210 | Δ*C. albicans* srb7::*C. albicans* ADE2 | Sandra Harris[3] |

[1]Hengartner etal.(1995)
[2]Unpublished
Young lab, Whitehead Institute, Cambridge, MA 02142
[3]Unpublished
Scriptgen Pharmaceuticals, Waltham, MA 02451

TABLE 3

Oligonucleotides

| Oligonucleotide | Sequence | |
|---|---|---|
| CaSRB7p15 | GGTATAGCGGCCGCGCCTGATATATCAATAGG | (SEQ ID NO:5) |
| CaSRB7p19 | GGTTCTCGAGCAATCGATGAAGAATCAAGTC | (SEQ ID NO:6) |
| CaSRB7p20 | GTCGACACAGCTACTAGTAATTAAGGAATGTTGG GTTAAG | (SEQ ID NO:7) |
| CaSRB7p21 | ACTAGTAGCTGTGTCGACGGTATAACCGAAACAA GAATATC | (SEQ ID NO:8) |
| CaADE2f | GGGCGCCTGCAGCGAACATATCTACTTTTCA | (SEQ ID NO:9) |
| CaADE2b | GGGCGCAGATCTGTTAGAGATGTGGT | (SEQ ID NO:10) |

REFERENCES FOR EXAMPLE

Bjorklund, S., and Kim, Y.-J. (1996). Mediator of transcriptional regulation. Trends Biochem. Sci. 21, 335–337.

Boeke, J., Truehart, J., Natsoulis, B., and Fink, G. R. (1987). 5-Flouro-orotic acid as a selective agent in yeast molecular genetics. Meth. Enzymol. 154, 164–175.

Brown, D. H., Slobodkin, I. V., and Kumamoto, C. A. (1996). Stable transformation and regulated expression of an inducible reporter construct in *Candida albicans* using restriction enzyme-mediated integration. Mol. Gen. Genet. 251, 75–80.

Chao, D. M., Gadbois, E. L., Murray, P. J., Anderson, S. F., Sonu, M. S., Parvin, J. D., and Young, R. A. (1996). A mammalian SRB protein associated with an RNA polymerase II holoenzyme. Nature 380, 82–85.

Elble R. (1992). A simple and efficient procedure for transformation of yeasts. Biotechniques 13, 18–20.

Farrell, S., Simkovich, N., Wu, Y., Barberis, A., and Ptashne, M. (1996). Gene activation by recruitment of the RNA polymerase II holoenzyme. Genes Dev. 10, 2359–2367.

Fonzi, W. A., and Irwin, M. Y. (1993). Isogenic strain construction and gene mapping in *Candida albicans*. Genetics 134, 717–728.

Guthrie, C., and Fink, G. R. eds. (1991). Guide to Yeast Genetics and Molecular Biology. Academic Press, New York.

Hengartner, C. J., Thompson, C. M., Zhang, J., Chao, D. M., Liao, S.-M., Koleske, A. J., Okamura, S., and Young, R. A. (1995). Association of an activator with an RNA polymerase II holoenzyme. Genes Dev. 9, 897–910.

Kim, Y.-J., Bjorklund, S., Li, Y., Sayre, M. H., and Kornberg, R. D. (1994). A multiprotein mediator of transcriptional activation and its interaction with the C-terminal repeat domain of RNA polymerase II. Cell 77, 599–608.

Koleske, A. J., Buratowski, S., Nonet, M., and Young, R. A. (1992). A novel transcription factor reveals a functional link between the RNA polymerase II CTD and TFIID. Cell 69, 883–894.

Koleske, A. J., and Young, R. A. (1994). An RNA polymerase II holoenzyme responsive to activators. Nature 368, 466–469.

Koleske, A. J., and Young, R. A. (1995). The RNA polymerase II holenzyme and its implications for gene regulation. Trends Biochem. Sci. 20, 113–116.

Liao, S.-M., Zhang, J., Jeffery, D. A., Koleske, A. J., Thompson, C. M., Chao, D. M., Viljoen, M., van Vuuren, H. J. J., and Young, R. A. (1995). A kinase-cyclin pair in the RNA polymerase II holoenzyme. Nature 374, 193–196.

Maldonado, E., Shiekhattar, R., Sheldon, M., Cho, H., Drapkin, R., Rickert, P., Lees, E., Anderson, C. W., Linn, S., and Reinberg, D. (1996). A human RNA polymerase II complex associated with SRB and DNA-repair proteins. Nature 381, 86–89.

Myers, L. C., Gustafsson, C. M., Bushnell, D. A., Lui, M., Erdjument-Bromage, H., Tempst, P., and Kornberg, R. D. (1998) The med proteins of yeast and their function through the RNA polymerase II carboxy-terminal domain. Genes Dev. 12, 45–54.

Nonet, M. L., and Young, R. A. (1989). Intragenic and extragenic suppressors of mutations in the heptapeptide repeat domain of Saccharomyces cerevisiae RNA polymerase II. Genetics 123, 715–724.

Philippsen, P., Stotz, A., and Scherf, C. (1991). DNA of *Saccharomyces cerevisiae*. Meth. Enzymol. 194, 169–182.

Sambrook, J., Fritsch, E. F., and Maniatis, T. (1989). Molecular Cloning: A Laboratory Manual, Second Edition (Cold Spring Harbor, New York: Cold Spring Harbor Laboratory Press).

Schiestl, R. H. and Gietz, R. D. (1989). High efficiency transformation of intact yeast cells using single stranded nucleic acids as a carrier. Curr. Gent. 16, 339–346.

Scully, R., Anderson, S. F., Chao, D. M., Wei, W., Ye, L., Young, R. A., Livingston, D. M., and Parvin, J. D. (1997). BRCA1 is a component of the RNA polymerase II holoenzyme. Proc. Natl. Acad. Sci. USA 94, 5605–5610.

Sikorski, R. S., and Hieter, P. (1989). A system of shuttle vectors and yeast host strains designed for efficient manipulation of DNA in *Saccaromyces cerevisiae*. Genetics 122, 19–27.

Thompson, C. M., Koleske, A. J., Chao, D. M., and Young, R. A. (1993). A multisubunit complex associated with the RNA polymerase II CTD and TATA-binding protein in yeast. Cell 73, 1361–1375.

Thompson, C. M., and Young, R. A. (1995). General requirement for RNA polymerase II holoenzymes in vivo. Proc. Natl. Acad. Sci. USA 92, 4587–4590.

What is claimed is:

1. An isolated nucleic acid having the sequence depicted in FIG. 2, SEQ ID NO: 1.

2. An isolated nucleic acid that hybridize to a nucleic acid as defined in claim 1 under stringent hybridization conditions.

3. A nucleic acid vector comprising a nucleic acid as defined in claim 1 operably linked to a transcription regulatory element.

4. A cell comprising a vector as defined in claim 3.

5. A cell as defined in claim 4, wherein said cell is selected from the group consisting of a bacterial, fungal, insect and mammalian cell.

6. A method for producing a CaSRB-7 polypeptide, which comprises:
 (i) culturing a cell as defined in claim 5 under conditions suitable for the production of CaSRB-7 polypeptide; and
 (ii) recovering said polypeptide from said culture.

* * * * *